United States Patent [19]

Parker

[11] 4,238,630

[45] Dec. 9, 1980

[54] PRODUCTION OF AROMATIC HYDROCARBONS

[75] Inventor: David G. Parker, Wilton, England

[73] Assignee: Imperial Chemical Industries Limited, London, England

[21] Appl. No.: 28,362

[22] Filed: Apr. 9, 1979

[30] Foreign Application Priority Data

May 8, 1978 [GB] United Kingdom ............... 18268/78

[51] Int. Cl.³ .............................................. C07C 2/68
[52] U.S. Cl. ..................................... 585/467; 585/454
[58] Field of Search ............................... 585/454, 467; 252/455 Z

[56] References Cited

U.S. PATENT DOCUMENTS 4,104,319  8/1978  Kaeding ............................... 585/454

FOREIGN PATENT DOCUMENTS 1402981  8/1975  United Kingdom .
1525323  9/1978  United Kingdom .
1525423  9/1978  United Kingdom .
1536827  12/1978  United Kingdom .

*Primary Examiner*—C. Davis
*Attorney, Agent, or Firm*—Cushman, Darby & Cushman

[57] ABSTRACT

Alkylation of aromatic hydrocarbons, especially toluene methylation, is carried out in the presence of a catalyst comprising an aluminosilicate zeolite of the ZSM-5 type in which some or all of the protons of the zeolite have been replaced by monovalent cations. Preferably, the replacement cations are sodium ions, the catalyst preferably containing more than 2% by weight of sodium.

10 Claims, No Drawings

PRODUCTION OF AROMATIC HYDROCARBONS

This invention relates to the production of alkylaromatic hydrocarbons by alkylation of aromatic hydrocarbons.

According to the present invention a process for the alkylation of an aromatic hydrocarbon comprises contacting an aromatic hydrocarbon or a mixture comprising an aromatic hydrocarbon with an alkylating agent under reaction conditions which are effective for accomplishing alkylation of the aromatic hydrocarbon and in the presence of a catalyst comprising an aluminosilicate zeolite of the ZSM-5 type in which some or all of the protons of the zeolite have been replaced by monovalent cations. Preferably the monovalent cations are sodium cations.

The ZSM-5 family of zeolites includes those known as ZSM-5, ZSM-8, ZSM-11 and ZSM-12. A general description of the family is available in U.S. Pat. No. 3,775,501 and the above members are more particularly described in the following patent specifications:

ZSM-5: U.S. Pat. No. 3,702,886 and U.K. Pat. No. 1,161,974
ZSM-8: U.K. Pat. No. 1,334,243
ZSM-11: U.S. Pat. No. 3,709,979
ZSM-12: U.K. Pat. No. 1,365,317

Typically, the ZSM-5 family of zeolites can be defined by the following characteristics:

| | | |
|---|---|---|
| $SiO_2/Al_2O_3$ mole ratio | 5 to 100 | |
| port size | 6 to 6.5A | (corresponding to rings of 10 $SiO_4$ and $AlO_4$ tetrahedra) | in addition to their characteristic X-ray diffraction patterns which are set out in the appropriate patent specifications listed above.

Methods of preparation of the ZSM-5 family of zeolites are described in the patent specifications listed above and in other specifications. Hitherto, it has been the practice to keep the alkali metal content of the zeolites of the ZSM-5 family to as low a level as possible and certainly to less than 2% by weight, because it was believed that the presence of alkali metal cations suppressed or limited the catalytic properties of the zeolites. We have now found that the alkylation of aromatic hydrocarbons is appreciably improved by the use of a catalyst comprising a zeolite of the ZSM-5 family in which some or all the protons of the zeolite are replaced by monovalent cations. Preferably, the monovalent cation is an alkali metal cation, more preferably sodium. Preferably, the amount of the monovalent cation, for example sodium, in the zeolite is at least 1.5% by weight, more preferably greater than 2% by weight, for example in the range greater than 2 to 3% by weight.

For use in the process according to this invention the zeolite of the ZSM-5 family is converted from the form in which it is usually produced, usually the hydrogen form. It is treated so as to increase its content of monovalent cation, for example by repeated contact with a solution of an alkali metal compound, followed by filtration, washing, drying and calcining. For example, the sodium content of ZSM-5 zeolite can be increased by repeated contact of the zeolite with a 5% sodium chloride solution at 50° C., followed by filtration, thorough washing with water and then drying at 120° C. Finally, the treated zeolite may be calcined at 450° C. in air for a period of the order of 16 hours.

After use, it is preferred to regenerate the catalyst by heating in air, preferably at a temperature in the range of 400° to 500° C., for example at or around 450° C.

Examples of the hydrocarbons which may be alkylated using the process of this invention include, for example, toluene.

The preferred alkylating agents for use in the process of this invention are any one or more alcohols, for example methanol, alkylesters for example methyl esters, alkyl ethers, for example dimethylether and alkyl halides.

Suitably, the molar ratio of aromatic hydrocarbons to alkylating agent is in the range 0.1:1 to 10:1, more preferably in the range 0.2:1 to 5:1.

Preferred operating conditions for the process of this invention include a temperature in the range 300° to 800° C., more preferably in the range 400° to 600° C., a reaction pressure in the range 1 to 100 Bar, more preferably in the range 1 to 60 Bar, and a weight hourly space velocity (weight of feed per unit weight of catalyst per hour) in the range 0.05 to 40, more preferably in the range 0.1 to 30. In general, higher space velocities are used at higher reaction temperatures.

Optionally, the process of this invention is effected in the presence of hydrogen. Suitable mole ratios of hydrogen to the aromatic hydrocarbon lie in the range 0.1:1 to 20:1, more preferably in the range 1:1 to 10:1.

The process of the present invention is particularly applicable to the methylation of toluene to xylenes, suitable methylating agents for which include methanol and dimethylether.

The invention will now be described further with reference to the following Examples.

EXAMPLE 1

Preparation of sodium form of zeolite ZSM-5

106g silica (Syloid 266) was dissolved in 1250 ml of a 20% solution in water of tetrapropylammonium hydroxide by boiling at 100° C. for 2 hours under reflux. Then 12 g sodium aluminate in 252 ml water was added with stirring. The resultant mixture was charged to an autoclave and stirred at 150 r.p.m. and 150° C. for 144 hours. Thereafter, the autoclave was discharged and the solids recovered by filtration. The product was washed twice with 2 liters of hot water and then dried to yield a powder of ZSM-5 zeolite. The product was ion-exchanged three times with a 5% aqueous solution of ammonium chloride to yield a product, designated MS1, which had a sodium content of 0.053% by weight, an aluminum content of 4.2%, and a silicon content of 36.9%.

5 g of the powdered zeolite was contacted with 100 ml of a 5% aqueous solution of sodium chloride at 50° C. for 1 hour. The solid was recovered by filtration and the procedure was repeated twice. After the final filtration, the zeolite was thoroughly washed with water and then dried at 120° C. for 1 hour. This product, designated MS2, had a sodium content of 2.1% by weight, an aluminumcontent of 4.1% and a silicon content of 33.5% by weight.

The product was compacted into 1 to 2.5 mm diameter chips, 2 g of which were placed in a suitable reactor and heated in air at 450° C. for 16 hours.

EXAMPLE 2

Methylation of Toluene

A number of experiments were carried out using two zeolite products, MS1 and MS2, prepared as described in Example 1. A mixture containing toluene and methanol in a 2:1 molar ratio of toluene to methanol was passed over 2 g of the catalyst under test in a glass tubular reactor. The reaction conditions and results obtained using catalyst MS1 (ZSM-5 containing 0.053% sodium) are shown in Table 1. The catalyst was regenerated in air at 450° C. between runs.

The results obtained using catalyst MS2 (ZSM-5 containing 2.1% sodium) are shown in Table 2. The catalyst was regenerated in air at 450° C. between runs.

Referring to Table 1, it will be seen that at low weight hourly space velocities (WHSV) there is only slight selectivity to p-xylene beyond the equilibrium level of 23 to 23.5% p-xylene which would be expected at the temperatures used. At higher WHSV, the selectivity to para-xylene is greater but falls away with time. Molar selectivity to xylenes is broadly within the range 65 to 75%.

Referring to Table 2, it can be seen that even at low WHSV there is good selectivity to para-xylene. The selectivity is even better as the WHSV increases and the marked falling off with time of the selectivity noted wih catalyst MS1 is not apparent with catalyst MS2. It is believed, therefore, that ZSM-5 type catalysts of enhanced sodium content, and which are regenerated as described hereinbefore, are likely to have a longer useful life in catalysing alkylation of aromatic hydrocarbons than, for example, the hydrogen form of ZSM-5.

TABLE 1

| Run No: | Time on line (hrs) | Temp. (°C.) | WHSV (hr$^{-1}$) | Conversion toluene (wt. %) | Xylene distribution in product (%) | | | Xylene selectivity (Molar) % |
|---|---|---|---|---|---|---|---|---|
| | | | | | para | meta | ortho | |
| 1 | 2 | 450 | 4.7 | 30.9 | 26.3 | 51.9 | 21.9 | 64.4 |
| | 4 | 450 | 4.7 | 31.6 | 26.6 | 51.6 | 21.9 | 64.2 |
| | 6 | 450 | 4.7 | 30.5 | 28.1 | 50.2 | 21.7 | 64.0 |
| 2 | 2 | 450 | 28 | 12.6 | 52.8 | 27.7 | 19.6 | 71.3 |
| | 4 | 450 | 28 | 5.1 | 50.0 | 23.6 | 26.4 | 68.0 |
| | 6 | 450 | 28 | 2.3 | 46.0 | 24.7 | 29.3 | 56.9 |
| 3 | 2 | 500 | 28 | 6.7 | 53.9 | 24.5 | 21.6 | 71.4 |
| | 4 | 500 | 28 | 4.6 | 50.5 | 23.2 | 26.3 | 75.2 |
| | 6 | 500 | 28 | 2.1 | 43.8 | 26.0 | 30.2 | 78.6 |

TABLE 2

| Run No: | Time on line (hrs) | Temp. (°C.) | WHSV (hr$^{-1}$) | Conversion toluene (wt. %) | Xylene distribution in product (%) | | | Xylene selectivity (Molar) % |
|---|---|---|---|---|---|---|---|---|
| | | | | | para | meta | ortho | |
| 4 | 2 | 450 | 2.7 | 19.3 | 60.9 | 29.3 | 9.8 | 68.7 |
| | 4 | 450 | 2.7 | 17.2 | 62.6 | 27.3 | 10.1 | 74.1 |
| | 8 | 450 | 2.7 | 15.1 | 61.3 | 26.9 | 11.8 | 77.1 |
| | 12 | 450 | 2.7 | 14.1 | 60.9 | 26.0 | 13.2 | 76.1 |
| | 15 | 450 | 2.7 | 12.3 | 61.6 | 25.4 | 13.0 | 74.2 |
| | 18 | 450 | 2.7 | 11.9 | 60.7 | 25.2 | 14.1 | 74.6 |
| 5 | 2 | 450 | 28 | 6.6 | 57.7 | 24.7 | 17.6 | 74.5 |
| | 4 | 450 | 28 | 5.0 | 54.3 | 23.9 | 29.8 | 75.0 |
| | 6 | 450 | 28 | 3.9 | 51.9 | 24.0 | 24.0 | 80.6 |
| 6 | 2 | 500 | 2.7 | 16.5 | 67.3 | 24.9 | 7.8 | 69.7 |
| | 4 | 500 | 2.7 | 23.5 | 57.7 | 31.9 | 11.0 | 74.3 |
| | 6 | 500 | 2.7 | 22.1 | 56.4 | 31.7 | 11.7 | 74.1 |
| 7 | 2 | 500 | 4.5 | 18.4 | 63.0 | 27.0 | 10.1 | 77.1 |
| | 4 | 500 | 4.5 | 14.5 | 62.8 | 26.6 | 10.6 | 76.5 |
| | 6 | 500 | 4.5 | 12.4 | 63.3 | 25.3 | 11.5 | 76.2 |
| 8 | 2 | 500 | 6.5 | 13.9 | 68.5 | 23.5 | 8.1 | 77.8 |
| | 4 | 500 | 6.5 | 10.6 | 66.9 | 23.3 | 10.1 | 76.6 |
| | 6 | 500 | 6.5 | 8.6 | 65.2 | 22.4 | 12.4 | 75.9 |
| 9 | 2 | 500 | 13.3 | 8.6 | 72.7 | 19.1 | 8.2 | 78.0 |
| | 4 | 500 | 13.3 | 5.4 | 70.3 | 18.1 | 11.6 | 77.4 |
| | 6 | 500 | 13.3 | 4.1 | 67.0 | 18.7 | 14.3 | 75.8 |
| 10 | 1 | 500 | 28 | 6.7 | 86.1 | 7.0 | 6.1 | 79.0 |
| | 2 | 500 | 28 | 4.5 | 77.6 | 14.1 | 8.3 | 79.6 |
| | 4 | 500 | 28 | 3.3 | 74.8 | 14.8 | 10.5 | 79.5 |
| | 6 | 500 | 28 | 2.7 | 72.1 | 15.2 | 12.7 | 78.4 |
| 11 | 2 | 550 | 2.7 | 27.5 | 47.9 | 37.1 | 14.9 | 77.1 |
| | 4 | 550 | 2.7 | 27.5 | 49.8 | 35.4 | 14.8 | 77.9 |
| | 6 | 550 | 2.7 | 27.5 | 49.7 | 34.9 | 15.4 | 75.4 |
| 12 | 2 | 550 | 7 | 24.3 | 60.9 | 28.4 | 10.7 | 77.6 |
| | 4 | 550 | 7 | 19.9 | 58.1 | 28.8 | 13.0 | 77.9 |
| | 6 | 550 | 7 | 16.7 | 57.2 | 27.7 | 15.1 | 75.3 |
| 13 | 2 | 550 | 14 | 17.2 | 68.1 | 21.9 | 10.0 | 79.2 |
| | 4 | 550 | 14 | 12.8 | 67.9 | 21.1 | 11.0 | 79.6 |
| | 6 | 550 | 14 | 11.7 | 63.4 | 21.9 | 14.8 | 75.6 |
| 14 | 2 | 550 | 28 | 12.4 | 67.8 | 22.0 | 10.2 | 78.4 |
| | 4 | 550 | 28 | 9.4 | 68.1 | 19.8 | 12.1 | 76.7 |
| | 6 | 550 | 28 | 7.6 | 67.0 | 18.6 | 14.4 | 77.8 |

It can be seen therefore that for toluenemethylation, contrary to the teaching of the prior art, it is advantageous to use ZSM-5 zeolite of enhanced sodium content. Hitherto, it has been common practice in the zeolite art to reduce the sodium content of zeolites such as ZSM-5 to very low levels since it was felt that the presence of sodium was disadvantageous in reactions using catalysts based on these zeolites. The process of this invention illustrates that the presence of sodium need not be disadvantageous. The reasons for the enhanced selectivity to xylenes (and especially to para-xylene) using sodium ZSM-5 as catalyst are not fully understood but it is felt that one explanation may be that preparation of the zeolite in the manner described degrades tetrapropylammonium cations present in the internal structure of the zeolite but leaves external sodium cations unchanged. Thus active largely acid sites are formed internally but the external sites remain inactive. It is thought that the pore size of the zeolite leads to selective production of xylenes, especially para-xylene, at the internal sites and that the xylenes are thereafter unaffected by the neutralised, inactive external sites where normally, in the absence of sodium cations, one would expect the external sites to be active and cause conversion of the xylene mixture at least partially to the thermodynamic equilibrium compositions of xylenes. The form of ZSM-5 catalyst used in the process of this invention is therefore more selective than the hydrogen form of ZSM-5.

I claim:

1. A process for the alkylation of an aromatic hydrocarbon which comprises contacting the aromatic hydrocarbon or a mixture comprising an aromatic hydrocarbon with an alkylating agent under reaction conditions which are effective for accomplishing alkylation of the aromatic hydrocarbon and in the presence of a catalyst comprising an aluminosilicate zeolite of the ZSM-5 type in which some or all of the protons of the zeolite have been replaced by monovalent cations, wherein the amount of said monovalent cation in the zeolite is at least 2.0% by weight.

2. A process as claimed in claim 1 in which the monovalent cations comprise sodium cations.

3. A process as claimed in claim 1 in which the zeolite is ZSM-5, ZSM-8, ZSM-11 or ZSM-12.

4. A process as claimed in claim 1 in which the aromatic hydrocarbon to be alkylated is toluene.

5. A process as claimed in claim 1 in which the alkylating agent comprises an alcohol, an alkyl ester or an alkyl halide.

6. A process as claimed in claim 1 in which the molar ratio of aromatic hydrocarbons to alkylating agent is in the range 0.1:1 to 10:1.

7. A process as claimed in claim 1 in which the process is effected in the presence of hydrogen.

8. A process as claimed in claim 7 in which the mole ratio of hydrogen to aromatic hydrocarbon is in the range 0.1:1 to 20:1.

9. A process as claimed in claim 1 for the production of xylenes by methylation of toluene which comprises contacting toluene or a mixture comprising toluene with an alkylating agent selected from methanol, dimethylether and methyl halides at a temperature in the range 400° to 600° C., a pressure in the range 1 to 60 Bar, and at a weight hourly space velocity in the range 0.05 to 40 and in the presence of a catalyst comprising an aluminosilicate zeolite of the ZSM-5 type in which some or all of the protons of the zeolite have been replaced by sodium cations, the amount of sodium in the catalyst being greater than 2% by weight.

10. A process as claimed in claim 1, wherein said monovalent cations are alkali metal cations.

* * * * *